United States Patent [19]
Roos et al.

[11] Patent Number: 6,008,893
[45] Date of Patent: Dec. 28, 1999

[54] REVERSIBLE-FLOW CONDUIT SYSTEM

[75] Inventors: Häkan Roos; Kjell Magnusson, both of Uppsala, Sweden

[73] Assignee: Biacore AB, Uppsala, Sweden

[21] Appl. No.: 09/273,615

[22] Filed: Mar. 22, 1999

[51] Int. Cl.[6] .................................................. G01N 21/01
[52] U.S. Cl. ...................... 356/246; 356/440; 422/68.1; 422/100; 422/103; 435/287.3; 73/863.71; 73/863.81
[58] Field of Search .................................... 356/246, 440, 356/73, 344; 204/452, 454; 422/68.1, 81, 82, 100, 103; 435/287.3, 288.7, 287.4; 73/863.71, 863.72, 863.81, 864.91, 864.21

[56] References Cited

U.S. PATENT DOCUMENTS 5,313,264  5/1994  Ivarsson et al. ......................... 356/246
5,633,168  5/1997  Glasscock et al. ...................... 422/68.1
5,783,740  7/1998  Tawarayama et al. ................. 422/68.1

*Primary Examiner*—Hoa Q. Pham
*Attorney, Agent, or Firm*—Seed and Berry LLP

[57] ABSTRACT

Systems and methods for reversibly and controllably flowing a first and second fluid adjacent to one or more discrete sensing surfaces of a biosensor are disclosed herein. The systems utilize a flow-cell conduit adapted to flow the first and second fluids in either a first or second flow direction and in a manner such that the first and second fluids separately contact the one or more discrete sensing surfaces of the biosensor. The flow-cell conduit is operatively connected to both a two-fluid conduit and a single-fluid conduit via a valveless juncture. The system also comprises a selector valve for reversing the flow direction of the fluid within the flow-cell conduit.

20 Claims, 7 Drawing Sheets

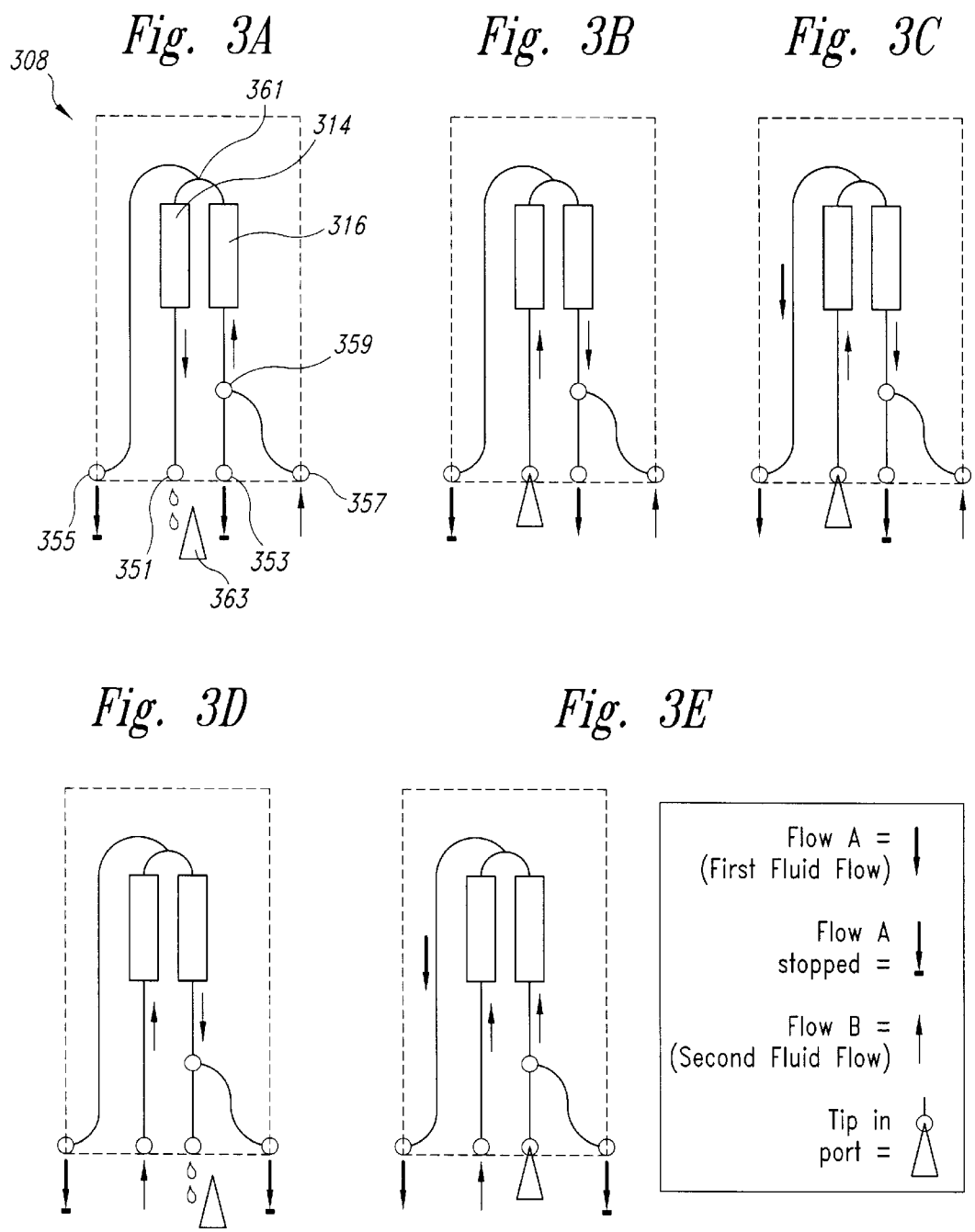

REVERSIBLE-FLOW CONDUIT SYSTEM

TECHNICAL FIELD

This invention relates generally to a reversible-flow conduit systems and, more specifically, to a conduit system for reversibly flowing a first and second fluid adjacent to one or more sensing surfaces of a biosensor.

BACKGROUND OF THE INVENTION

A variety of analytical techniques are used to characterize interactions between molecules, particularly in the context of assays directed to the detection of biomolecular interactions by use of a biosensor. For example, antibody-antigen interactions are of fundamental importance in many fields, including biology, immunology and pharmacology. In this context, many biosensor-based analytical techniques involve binding of a "ligand" (such as an antibody) to a solid support on a sensing surface (i.e., a sensitized surface on a sensor chip), followed by contacting the surface-bound ligand with an "analyte" (such as an antigen). The surface-bound ligand is generally contacted with the analyte by "flowing" directly adjacent thereto an analyte solution, where the analyte solution flows within a flow channel or conduit structure of the biosensor.

In this regard, there are a number of different classes of biosensor instrumentation designed to contact analyte and reagent solutions with one or more sensing surfaces. One representative class includes the affinity-based biosensors manufactured and sold by Biacore AB (Uppsala, Sweden) (hereinafter the "Biacore instrument"). The Biacore instrument utilizes surface plasmon resonance (SPR) technology and, in its simplest form, includes a light source such as a light emitting diode, a sensor chip covered with a thin gold film, a flow-cell conduit system for flowing sample and reagent solutions adjacent to a sensing surface on the sensor chip, and a photo detector. Incoming light from the diode is reflected in the gold film and detected by the photo detector. At a certain angle of incidence ("the SPR angle"), a surface plasmon wave is set up in the gold layer, which is detected as an intensity loss or "dip" in the reflected light. The change of light intensity is plotted as a "sensorgram." The theoretical basis behind such instrumentation has been fully described in the literature (see, e.g., Jönsson, U. et al., *Biotechniques* 11:620–627, 1991). One of the important features of this class of biosensors is that they are capable of detecting biomolecular interactions in real-time, without the need for radioactive labels or fluorescent tags. As a result, affinity-based biosensors are, in general, becoming much more popular in many biochemical research settings.

The SPR-based Biacore instrument employs optical-based sensors, which may be generally classified as a mass detection method. Other types of mass detection techniques include, but are not limited to, piezoelectric, thermo-optical and surface acoustic wave (SAW) methods. In addition, to mass detection methods, biosensor instruments may also employ electrochemical methods, such as potentiometric, conductometric, amperometric and capacitance methods. However, regardless of the detection method utilized in a specific instrument, sample must be brought into contact with the sensing surface and, after the detection is complete, must be removed from the sensing surface to permit analysis of additional sample, and/or to permit cleaning or regeneration of the sensing surface.

Methods for contacting a sample to a biosensor surface varies widely. For example, the Biacore instrument delivers sample to the sensor chip by means of an integrated microfluidic cartridge. A typical microfluidic cartridge consists of a series of precision-cast channels in a hard silicon polymer plate which forms one or more flow paths for buffer and sample delivery. A set of pneumatically actuated diaphragm valves directs fluid flow through the various channels to the sensing surfaces of the biosensor. In this manner, single or multichannel analysis is permitted. Other sample delivery techniques, such as "hydrodynamic injection" and "continuous flow injection," typically include tubing along with appropriate pumps, or aspiration of the sample onto the sensor surface.

Regardless of the sample delivery technique employed, the injection performance in terms of low dispersion is correlated to minimizing the dead volume. In commercially available systems, like the Biacore instrument, the "dead volume" is defined by the distance (which equates to volume) between the detector and the valve; the further away the valve is from the sensing surface the greater the dead volume (see, e.g., Ruzicka J. and Hansen E., *Flow Injection Analysis,* John Wiley & Sons, New York, 1988).

Although a number of techniques have been employed to deliver sample to the surface of a biosensor, as well as to remove sample from the surface, there is still a need in the art for improvements to such delivery systems. For example, an improved sample deliver system should be capable of contacting sample and/or reagent solutions to one or more sensing surfaces of the biosensor so as to optimally conserve sample and/or reagent solutions. Moreover, reducing the dead volume or the time delay associated with contacting a plurality of solutions, such as buffer, sample, and regeneration solutions, with the one or more sensing surfaces of the biosensor would be desirable.

Accordingly, there is a need in the art for an improved biosensor flow conduit systems, as well as to methods and apparatus related thereto. The present invention fulfills these needs, and provides further related advantages.

SUMMARY OF THE INVENTION

In brief, the present invention is directed to reversible-flow conduit systems for delivery of a liquid to the sensing surface of a biosensor and, more specifically, to a flow conduit system for reversibly flowing a first fluid and a second fluid adjacent to one or more discrete sensing surfaces of a biosensor. In one embodiment, the first fluid is the liquid sample to be detected by the biosensor, while the second fluid is a solution for regenerating the biosensor surface.

The reversible-flow conduit system of the present invention comprises a flow-cell conduit, a single-fluid conduit, a two-fluid conduit and at least one selector valve.

The flow-cell conduit includes first and second inlet/outlet ports at respective first and second end portions of the flow-cell conduit, wherein the first inlet/outlet port is adapted to receive a first fluid or expel a second fluid, and the second inlet/outlet port is operatively connected to a valveless juncture. The flow-cell conduit is adapted to flow the first fluid and the second fluid in either a first or second flow direction such that the first and second fluids are capable of separately contacting the one or more discrete sensing surfaces of the biosensor. The first flow direction corresponds with a first flow path defined by a flow from the first inlet/outlet port to the second inlet/outlet port, while the second flow direction corresponds with a second flow path defined by a flow from the second inlet/outlet port to the first inlet/outlet port.

The single-fluid conduit is adapted to flow therein the second fluid in the second flow direction, wherein the single-fluid conduit has first and second single-fluid conduit end portions, wherein the first single-fluid conduit end portion is operatively connected to the valveless juncture to thereby allow passage of the second fluid there-through and into the second inlet/outlet port of the flow-cell conduit and/or into a second two-fluid conduit end portion.

The two-fluid conduit is adapted to simultaneously flow therein the first and second fluids in the first flow direction, wherein the two-fluid conduit has first and second two-fluid conduit end portions, wherein the first two-fluid conduit end portion is operatively connected to the valveless juncture to thereby allow passage of the first and second fluids there-through and into the second two-fluid conduit end portion.

The selector valve includes first and second positions adapted to controllably reverse the flow direction of the first and second fluids in the flow-cell conduit, wherein the selector valve is interposed between the first and second two-fluid conduit, and wherein the first fluid is capable of continuously flowing in the flow-cell conduit in the first flow direction when the selector valve is in the first position, and wherein the second fluid is capable of continuously flowing in the flow-cell conduit in the second direction when the selector valve is in the second position.

In another embodiment, an apparatus is disclosed comprising the reversible-flow conduit system of the present invention. The apparatus comprises, in addition to the reversible-flow conduit system, a biosensor having a light source and a detector. In yet another embodiment, a method is disclosed for reversing the flow direction of a fluid in a flow-cell of a biosensor by a actuating a selector valve associated with a reversible-flow conduit system.

These and other aspects of the present invention will be evident upon reference to the following detailed description and related Figures.

BRIEF DESCRIPTION OF THE DRAWINGS

FIG. 3A is partial view of FIG. 3 depicting a first flow pattern through first and second flow-cell flow channels.

FIG. 3B is partial view of FIG. 3 depicting a second flow pattern through first and second flow-cell flow channels.

FIG. 3C is partial view of FIG. 3 depicting a third flow pattern through first and second flow-cell flow channels.

FIG. 3D is partial view of FIG. 3 depicting a fourth flow pattern through first and second flow-cell flow channels.

FIG. 3E is partial view of FIG. 3 depicting a fifth flow pattern through first and second flow-cell flow channels.

DETAILED DESCRIPTION OF THE INVENTION

As mentioned above, this invention is directed to reversible or split-flow flow conduit systems associated with biosensors and, more specifically, to a reversible-flow conduit system for reversibly flowing a first and second fluid adjacent to one or more discrete sensing surfaces of a biosensor. The present invention is also directed to methods of operation associated with such reversible-flow conduit systems. Although many specific details of certain embodiments of the invention are set forth in the following detailed description and accompanying Figures, those skilled in the art will recognize that the present invention may have additional embodiments, or that the invention may be practiced without several of the details described herein.

In the several embodiments set forth below, the inventive reversible or split-flow injection systems are understood to be adapted for use with "biosensors." As is appreciated by those skilled in the art, biosensors are analytical devices for analyzing minute quantities of sample solution having an analyte of interest, wherein the analyte is analyzed by a detection device that may employ a variety of detection methods. Typically, such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers. One exemplary biosensor is disclosed in U.S. Pat. No. 5,313,264 (assigned to Biacore AB, Uppsala, Sweden), which is incorporated herein by reference in its entirety.

Figure 1:
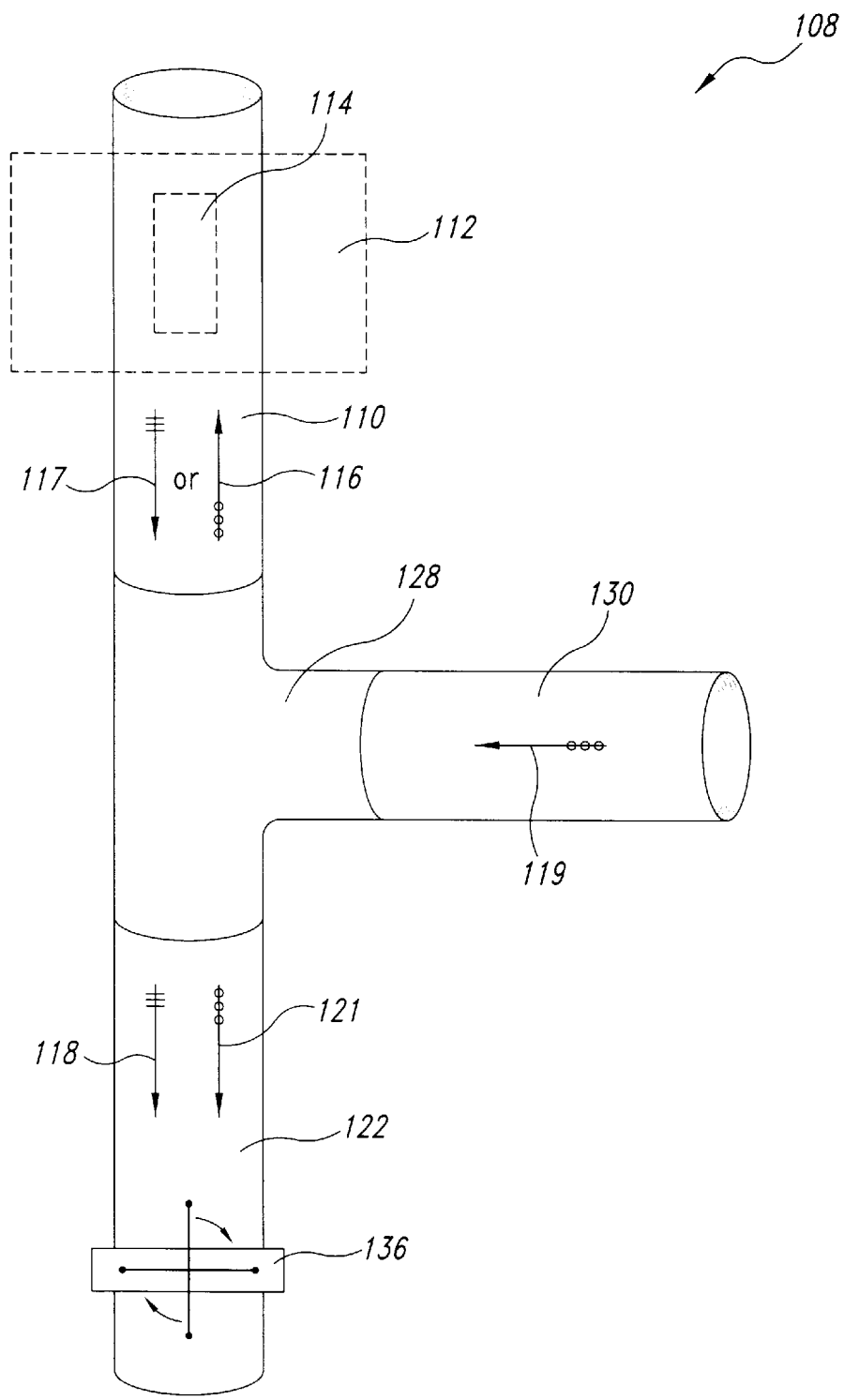
FIG. 1 is a schematic illustration of a reversible-flow conduit system of the present invention.

In one embodiment of the present invention, and as best seen in FIG. 1, a reversible-flow conduit system 108 includes a flow-cell conduit 110 integral with a flow cell 112 of a biosensor (not shown), wherein the flow cell 112 has a discrete sensing surface 114. The flow-cell conduit 110 is connected to both a two-fluid conduit 122 and a single-fluid conduit 130 via a valveless juncture 128. The valveless juncture 128 allows the flow-cell conduit 110 to communicate with both the two-fluid conduit 122 and the single-fluid conduit 130; the valveless juncture 128 also allows the two-fluid conduit 122 to communicate with the single-fluid conduit 130. In other words, the flow-cell conduit 110, the two-fluid conduit 122, and the single-fluid conduit 130 all communicate with one another via the valveless juncture 128.

The reversible-flow conduit system 108 also includes a selector valve 136 interposed between the ends of the two-fluid conduit 122. The selector valve 136 may be in either an open position or a closed position. When the selector valve 136 is in the open position, a first fluid (depicted by arrow 117) from the flow-cell conduit 110 and a second fluid (depicted by arrow 119) from the single-fluid conduit 130 may flow within the two-fluid conduit 122 as depicted by arrows 118 and 121. When the selector valve 136 is in the closed position, no fluid may flow within the two fluid conduit 122; however, the second fluid (depicted by arrow 119) from the single-fluid conduit 130 may flow within the flow-cell conduit 110 as depicted by arrow 116. By alternating between the open and closed positions, the flow direction of a fluid within the flow-cell conduit 110 may be controllably reversed.

Figure 2A:
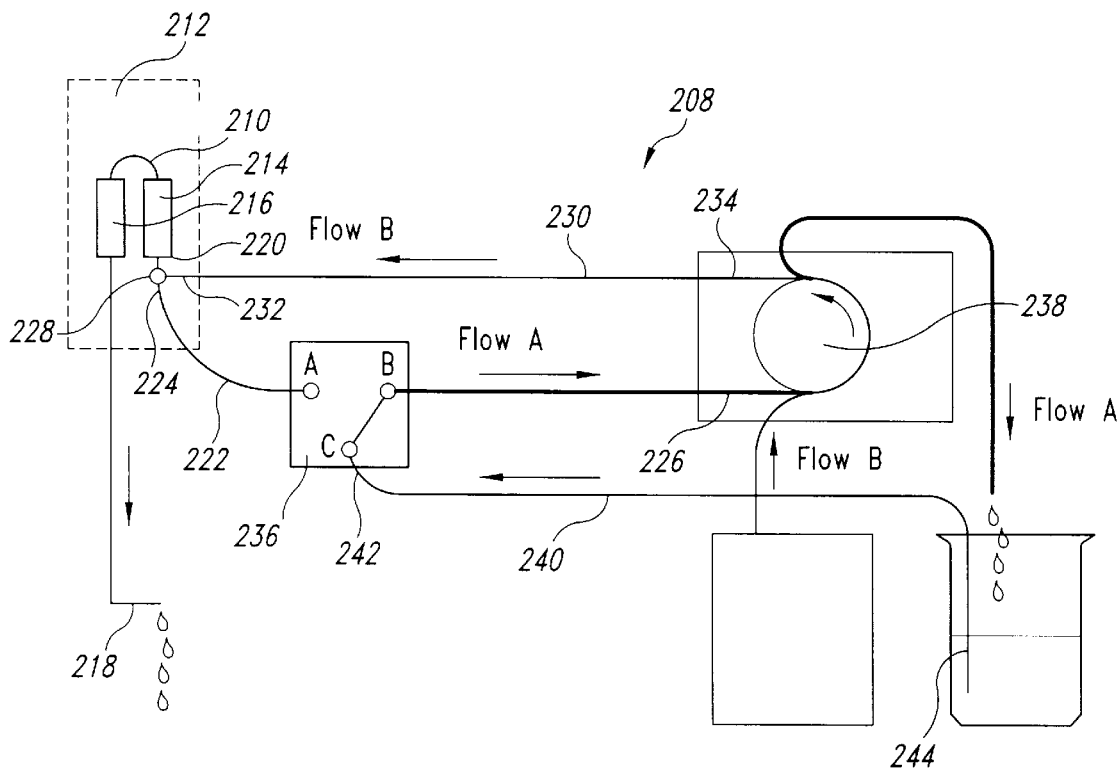
FIG. 2A is a schematic illustration of a reversible-flow conduit system having a selector valve in a second position ("baseline and washout") to thereby allow a second fluid to continuously flow in a flow-cell conduit in a second direction in accordance with an embodiment of the present invention.

In another embodiment of the present invention, and as best seen in FIG. 2A, a reversible-flow conduit system 208 includes a flow-cell conduit 210 integral with a flow cell 212 of a biosensor (not shown), wherein the flow cell 212 has one or more discrete sensing surfaces, 214 and 216, respectively. The flow-cell conduit 210 is adapted to flow a sample solution having an analyte of interest (e.g., a first fluid) and a buffer or regeneration solution (e.g., a second fluid) in either direction along the flow-cell conduit 210; that is, first and second fluids may flow within the flow-cell conduit 210 in either a first or second direction. In addition, the flow-cell conduit 210 is also adapted to flow the first and second fluids in a manner such that they separately contact (i.e., the two fluids do not substantially mix) the one or more discrete sensing surfaces (214 and 216, respectively). The flow-cell conduit 210 also has first and second inlet/outlet ports, 218 and 220, respectively, at its respective first and second ends; the first inlet/outlet port 218 is adapted to receive a liquid sample or expel a liquid waste. The first inlet/outlet port 218 may also adapted to engageably receive a pipette tip or syringe needle.

As also seen in FIG. 2A, the reversible-flow conduit system 208 also includes a two-fluid conduit 222 that is adapted to simultaneously flow the first and second fluids in the first flow direction. The two-fluid conduit 222 has first and second two-fluid conduit end portions, 224 and 226, respectively, wherein the first two-fluid conduit end portion 224 is operatively connected to the second inlet/outlet port 220 of the flow-cell conduit 210 at a valveless juncture 228 to thereby allow passage of the first and second fluids. In other words, the valveless juncture 228 allows the flow-cell conduit 210 to communicate with the two-fluid conduit 222. As depicted, the flow-cell conduit 210 communicates with the two-fluid conduit 222 along their respective longitudinal axes.

The reversible-flow conduit system 208 also includes a single-fluid conduit 230 that is adapted to flow the second fluid in the second direction. The single-fluid conduit 230 has first and second single-fluid conduit end portions, 232 and 234, respectively, wherein the first single-fluid conduit end portion 232 is operatively connected to the valveless juncture 228 associated with the second inlet/outlet port 220 and the first two-fluid conduit 222 to thereby allow passage of the second fluid. In other words, the valveless juncture 228 not only allows the flow-cell conduit 210 to communicate with the two-fluid conduit 222, it also allows the flow-cell conduit 210 to communicate with the single-fluid conduit 230—thus, the flow-cell conduit 210, the two-fluid conduit 222, and the single-fluid conduit 230, all communicate with one another via the valveless juncture 228. As depicted, the flow-cell conduit 210 communicates with the two-fluid conduit 222 along their respective longitudinal axes, whereas the single-fluid conduit 230 communicates transversely with respect thereto.

Figure 2B:
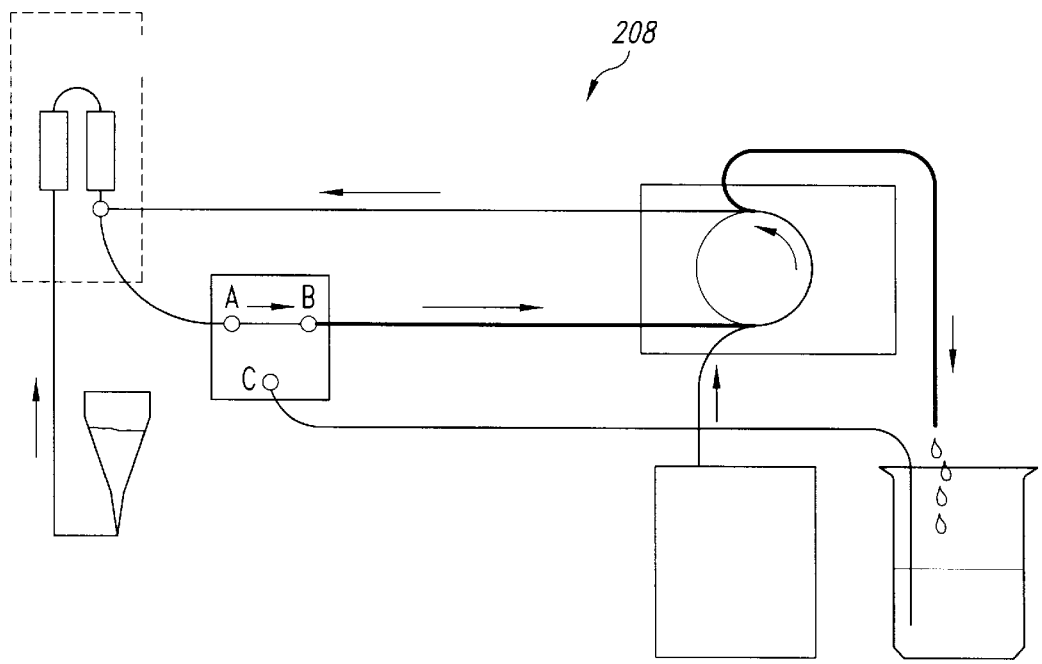
FIG. 2B is a schematic illustration of a reversible-flow conduit system of FIG. 2A having the selector valve in a first position ("injection") to thereby allow a first fluid to continuously flow in the flow-cell conduit in a first direction in accordance with an embodiment of the present invention.

Finally, and as also seen in FIG. 2A and FIG. 2B, the reversible-flow conduit system 208 also includes a selector valve 236 that is adapted to controllably reverse the flow direction of the first and second fluids (depending upon which fluid is present) within the flow-cell conduit 210. The selector valve 236 is interposed between the end portions 224, 226 of two-fluid conduit 222. As shown, the selector valve 236 has a first and second position: the first fluid is capable of continuously flowing in the flow-cell conduit 210 in the first flow direction (denoted as "Flow A") when the selector valve 236 is in the first position (denoted by a connecting line between points A and B in FIG. 2B), and the second fluid is capable of continuously flowing in the flow-cell conduit 210 in the second direction (denoted as "Flow B") when the selector valve is in the second position (denoted by a connecting line between points B and C in FIG. 2A).

In operation, and as shown in FIG. 2A, a buffer solution (e.g., a second fluid) is continuously flowing in the flow-cell conduit 210 in the second flow direction (i.e., Flow B) because the selector valve 236 is in the second position (the buffer solution is being discharged or expelled from the first inlet/outlet port 218 as a waste). In comparison, and as shown in FIG. 2B, a sample solution (e.g., a first fluid) is continuously flowing in the flow-cell conduit 210 in the first flow direction (i.e. Flow A) because the selector valve 236 is in the first position (the sample solution is being injected into the first inlet/outlet port 218). By selective use of the selector valve 236, the amount of sample and/or reagent solution used for analytical purposes may be conserved, and the time delay associated with contacting the first and second fluids (e.g., buffer, sample, and regeneration solutions) with the one or more sensing surfaces of the biosensor may be reduced.

In another embodiment and as best seen in FIG. 2A, the reversible-flow conduit system 208 of the present invention also includes a pump 238 that is operatively connected to the second end portion 226 of the two-fluid conduit 222, and to the second end portion 234 of the single-fluid conduit 230. The pump 238 may be a peristaltic pump that has first and second pumping channels (not shown) operatively connected to the respective second end portions 226, 234 of the respective two-fluid and single-fluid conduits 222, 230. The first and second pumping channels may be two tubes mounted on the peristaltic pump, wherein the two tube have different inner diameters to effectuate different flow rates. The pump 238 may alternatively be a first and second syringe pump similarly connected to the respective second end portions 226, 234 of the respective two-fluid and single-fluid conduits 222, 230. As is appreciated by those skilled in the art, peristaltic and syringe pumps are widely available from a variety of commercial sources.

In general, the volumetric flow rate capacity of the two-fluid conduit 222 equals the sum of the volumetric flow rate capacity of the flow-cell conduit 210 and the single-fluid conduit 230. Thus, and when the selector valve 236 is in the first position, a buffer solution flowing at a typical flow rate of 25 $\mu$l/min may combine, at the valveless juncture 228, with a sample solution likewise flowing at a typical flow rate of 25 $\mu$l/min to thereby yield a sample/buffer solution flowing within the two-fluid conduit 222 at a combined flow rate of 50 μl/min. (Note that the combined sample/buffer solution flows only in the first flow direction.) Although the above numerical flow rate capacities are representative, it should be understood that such capacities may fall anywhere within the range of operable volumetric flow rates associated with the biosensor.

In another embodiment and as best seen in FIG. 2A, the reversible-flow conduit system of the present invention includes a waste-fluid conduit 240 adapted to flow a waste fluid in a circular manner within the reversible-flow conduit system 208. The waste-fluid conduit 240 has first and second conduit end portions, 242 and 244, respectively, wherein the first waste-fluid conduit end portion 242 is operatively connected to the selector valve 236 such that the waste fluid circularly flows within the reversible-flow conduit system 208 when the selector valve is in the second position as shown.

Figure 3:
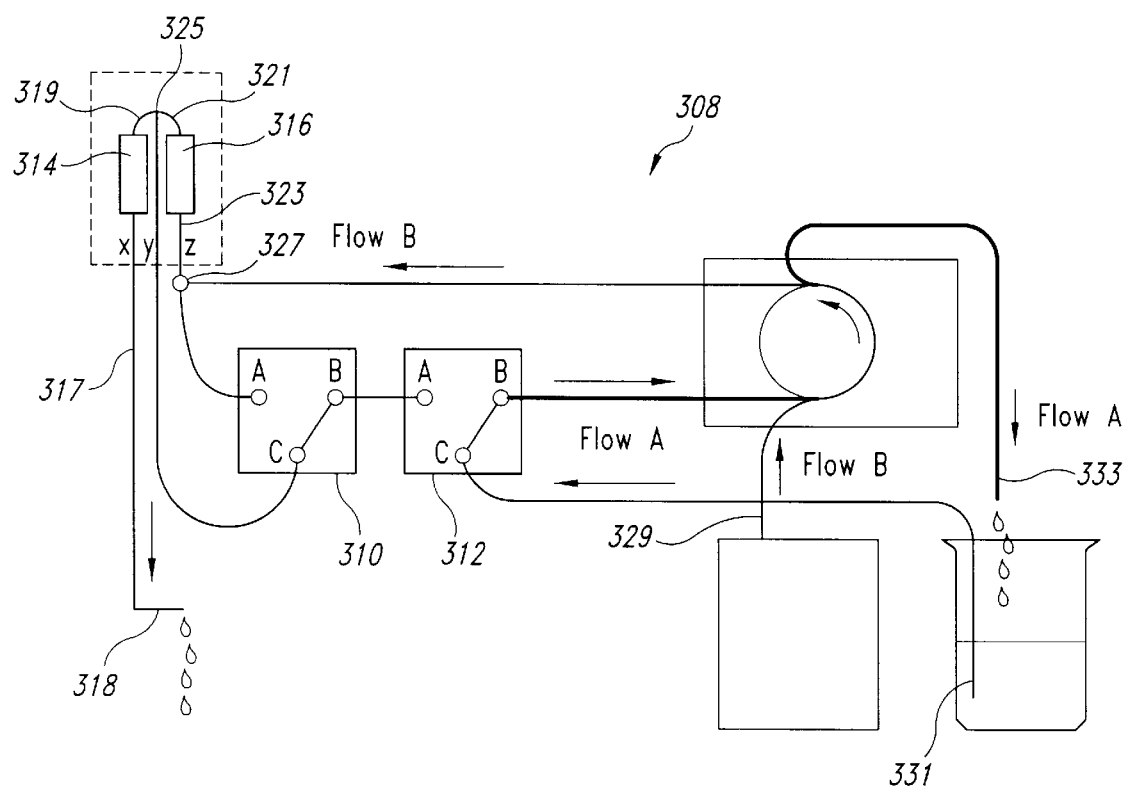
FIG. 3 is a schematic illustration of a reversible-flow conduit system having first and second selector valves for controllably reversing the flow direction of liquids flowing within first and second flow-cell flow channels.

In yet another embodiment of the present invention and as best seen in FIG. 3, a reversible-flow conduit system 308 includes a first selector valve 310 and a second selector valve 312. In combination, the first and second selector valves 310, 312 allow for controllably reversing the flow direction of liquids flowing within a first flow-cell flow channel 314 and a second flow-cell flow channel 316 independently from each other. In accordance with this embodiment, individual flow cells (and hence sensing surfaces) can be addressed separately for purposes of ligand immobilization, analyte detection, and/or surface regeneration. Exemplary flow patterns associated with the first and second flow-cell flow channels 314, 316 which are effectuated by different combinations of flow positions of the first and second selector valves 310, 312 are depicted in FIGS. 3A–E. (Note that these various flow patterns allow individual flow cells to be separately addressed with a plurality of different solutions.)

More specifically, FIG. 3A depicts a first flow pattern in which a second fluid (e.g., a running buffer) is continuously flowing through the first and second flow-cell flow channels 314, 316 (and hence adjacent to their respective sensing surfaces) in series. As depicted, there are two inlet/outlet ports 351, 353 for the first and second fluids, an outlet/stop port 355, and an inlet/stop port 357. This first flow pattern corresponds to introducing (e.g., pumping) the second fluid into an open inlet/stop port 357, while the first inlet/outlet port 351 is open and while the second inlet/outlet port 353 and the outlet/stop port 355 are both closed. In this configuration and as shown, the second fluid may flow continuously through a first and second valveless juncture 359, 361 of the reversible-flow conduit system 308 before being expelled out of the first inlet/outlet port 351.

FIG. 3B depicts a second flow pattern in which a first fluid (e.g., a sample solution) is continuously flowing through the first and second flow-cell flow channels 314, 316 (and hence adjacent to their respective sensing surfaces) in series. This second flow pattern corresponds to introducing the second fluid into an open inlet/stop port 357 and at the same time introducing (e.g., injecting) the first fluid into an open first inlet/outlet port 351 via a pipette tip 363, while the outlet/stop port 355 is closed and while the second inlet/outlet port 353 is open. In this configuration and as shown, the first fluid may flow continuously through the first flow-cell flow channel 314, the second valveless juncture 361, the second flow-cell flow channel 316, and the first valveless juncture 359 before being expelled out of (together with the second fluid) the second inlet/outlet port 353.

FIG. 3C depicts a third flow pattern in which a first fluid is continuously flowing through the first flow-cell flow channel 314 and a second fluid is continuously flowing through the second flow-cell channel 316. This third flow pattern corresponds to introducing the second fluid into an open inlet/stop port 357 and at the same time introducing the first fluid into an open first inlet/outlet port 351 via a pipette tip 363, while the outlet/stop port 355 is open and while the second inlet/outlet port 353 is closed. In this configuration and as shown, the first fluid may flow continuously through the first flow-cell flow channel 314 while the second fluid may flow continuously through the second flow-cell flow channel 316. The first and second fluids then combine at the second valveless juncture 359 before being expelled out of the second inlet/outlet port 353.

FIG. 3D depicts a fourth flow pattern in which a first fluid (e.g., a regeneration or wash solution) is continuously flowing through the first and second flow-cell flow channels 314, 316 (and hence adjacent to their respective sensing surfaces) in series. This fourth flow pattern corresponds to introducing the first fluid into an open first inlet/outlet port 351, while the second inlet/outlet port 353 is open and while the outlet/stop port 355 and the inlet/stop port 357 are both closed. In this configuration and as shown, the first fluid may flow continuously through the first flow-cell flow channel 314, the second valveless juncture 361, the second flow-cell flow channel 316, and the first valveless juncture 359 before being expelled out of the second inlet/outlet port 353.

FIG. 3E depicts a fifth flow pattern in which a first fluid is continuously flowing through the first flow-cell flow channel 314 and a second fluid is continuously flowing through the second flow-cell channel 316. This fifth flow pattern corresponds to introducing the first fluid into an open first inlet/outlet port 351 and at the same time introducing the second fluid into an open second inlet/outlet port 353 via a pipette tip 363, while the outlet/stop port 355 is open and while the inlet/stop port 357 is closed. In this configuration and as shown, the first fluid may flow continuously through the first flow-cell flow channel 314 while the second fluid may flow continuously through the second flow-cell flow channel 316. The first and second fluids combine at the second valveless juncture 359 before being expelled out of the second inlet/outlet port 353.

Figure 4:
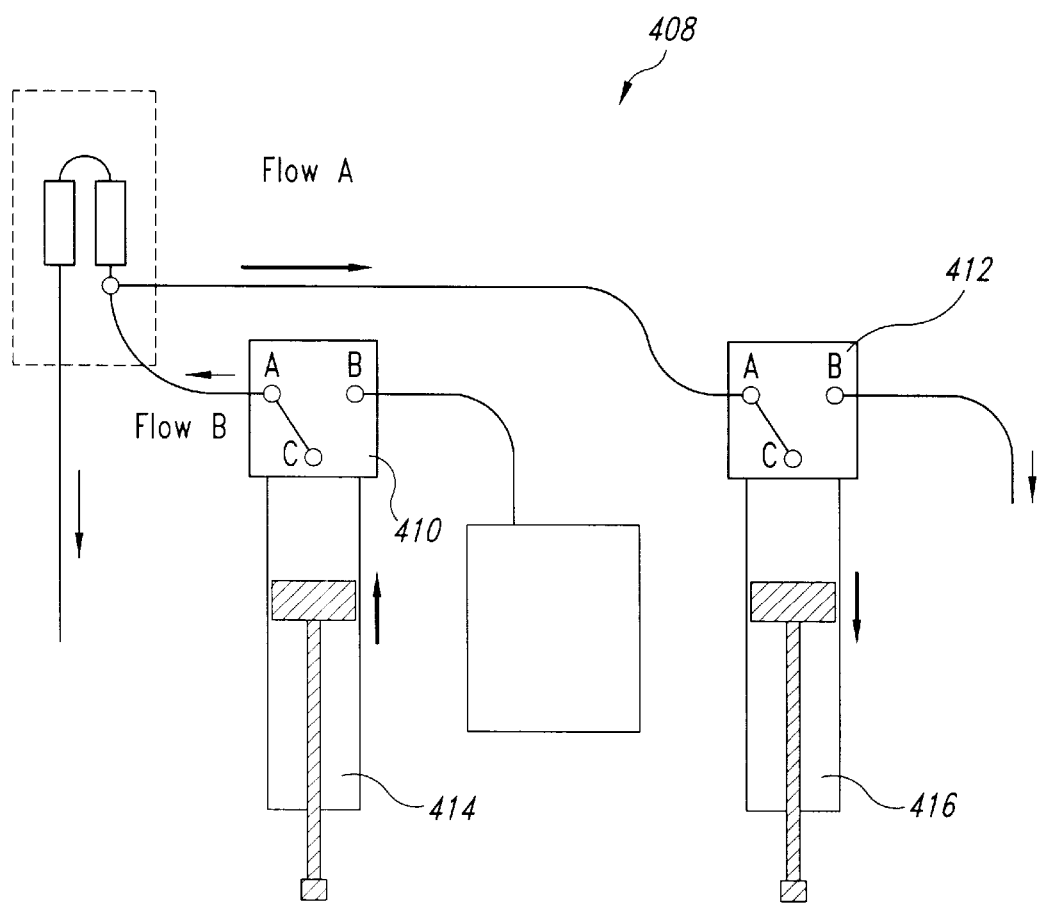
FIG. 4 is a schematic illustration of a reversible-flow conduit system having first and second selector valves for controllably reversing the flow direction of liquids flowing within first and second flow-cell flow channels operatively connected to respective first and second syringe pumps.

In still another embodiment and as best seen in FIG. 4, a reversible-flow conduit system 408 includes first and second selector valves 410, 412 operatively connected to respective first and second syringe pumps 414, 416. This configuration may improve some aspects associated with pumping various solutions over a two channel peristaltic pump in that the dead-volume between the flow cell and the split (e.g., flow connecting point or valveless juncture) may be decreased.

Based the foregoing detailed description and accompanying Figures, it should be recognized that the present invention provides for certain advantages over the prior art, advantages such as the following: (1) permits low dispersion injections to one or more sensing surfaces without valves integrated close to the flow cell; (2) allows baseline buffer and wash solution to be the same (i.e., no need for separate washing procedures); (3) allows a pipette tip to operate as a disposable loop (or the sample vial itself if the injection port is a needle); and (4) provides for a robust delivery system that has few components, but is nevertheless easy to control and automate.

For purposes of illustration and not limitation, the following example more specifically discloses various aspects of the present invention.

EXAMPLE

This example illustrates how a representative embodiment of the present invention may be used to reversibly flow running buffers, reagents, and sample solutions within the flow cells of a biosensor.

Material and Methods

A BIACORE® X instrument (Biacore AB, Uppsala, Sweden) was modified with a redesigned flow system, a schematic illustration of which is shown in FIG. 3. An integrated fluid cartridge containing two flow cells 314, 316, four flow channels 317, 319, 321, 323, and two connection points (splits) 325, 327 was used together with a connector block (not shown) having three tube inlets/outlets 329, 331, 333 and one combined injector and waste port 318. Thus, the original syringe pump module of the BIACORE® X was exchanged with a two channel peristaltic pump 338 and two selector valves 310, 312.

Sensor chip CM5 (research grade), rabbit anti-mouse IgG1 (RAMg1), Hepes buffer saline (HBS-EP) and amine coupling kit were obtained from Biacore AB (Uppsala Sweden). Monoclonal anti-p24 antibodies (Mabs) were from Pharmacia Diagnostics AB (Uppsala, Sweden) and HIV-1 core protein p24 was from Pharmacia Genetic Engineering (San Diego, U.S.A.).

Explanation of Injection Procedure

Sensor surface preparation and analysis all involved a sequence of liquid injections into the sample and reagent solution delivery system. The injection started by establishing a baseline with running buffer (shown as Flow B in FIG. 3), which meant that selector valve 312 was in position B-C (selector valve 310 could have been in either positions). The running buffer first entered flow cell 316, proceeded to flow cell 314, and was then expelled via the combined waste and injection port 318. Injection of sample and reagents was performed by placing a pipette tip containing the sample/reagent in the injection port 318 and activating selector valves 310 and 312 to the A-B positions. Flow A, which has a higher flow rate than Flow B, drew both the sample from the pipette tip and the running buffer flowing as Flow B. The injection of sample was stopped by switching back selector valve 312 to position B-C such that the baseline buffer (Flow B) rinsed the two flow cells 314, 316 and four flow channels 317, 319, 321, 323 thereby establishing a new baseline. The selector valve 310 was used to either direct the sample over both flow cells 314, 316 or over only flow cell 3214.

Preparation of Sensor Chips

During immobilization of the ligand, RAMg1, the flow from the combined waste and injection port 318 was directed only over flow cell 314 by activating selector valve 310 to position B-C and selector valve 312 to position A-B. During baseline and wash out, the selector valves 310 and 312 were in positions B-C and B-C, respectively.

Figure 5:
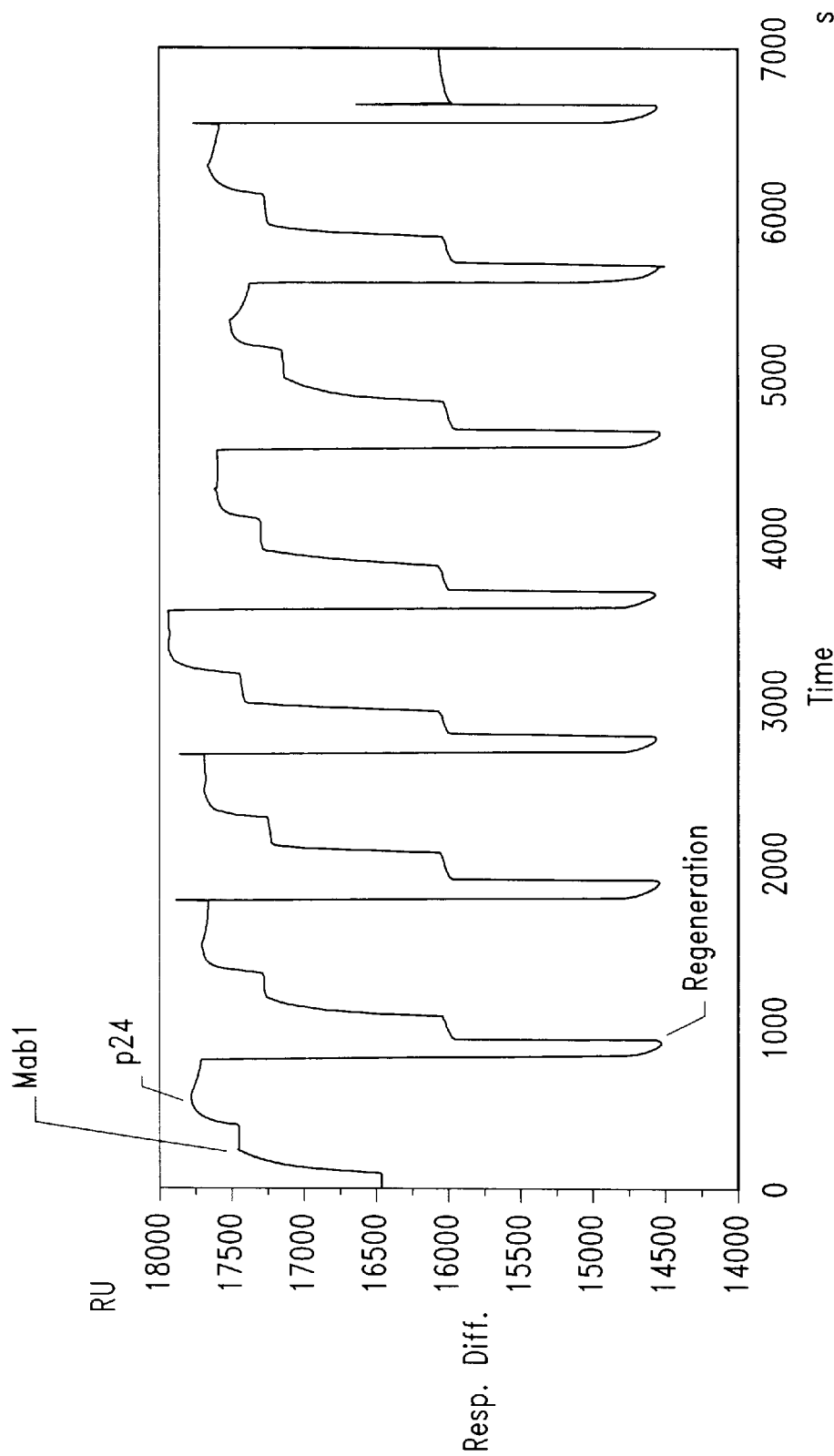
FIG. 5 is a sensorgram illustrating the biomolecular interactions and regeneration of seven Mabs with a surface-bound receptor.

The standard protocol for immobilization of RAMg1 recommended by Biacore AB was used resulting in an immobilization amount of 15609 resonance units (RU) in flow cell 314 as is shown in the sensorgram of FIG. 5. The flow rate was approximately 15 μl/min (Flow A≈30 μl/min and Flow B≈15 μl/min) and approximately 120 μl RAMg1 solution at 50 μg/ml concentration was consumed (i.e., totally 6 μg RAMg1). (Note that the RAMg1 surface can capture all monoclonal antibodies of subclass G1.)

Capturing of Mabs to Sensor Chips

The Mabs were diluted in HBS-EP to a final concentration of approximately 10 μg/ml. Each Mab was captured to a level of about 1200 RU in flow cell 314. The level was controlled by varying the contact time. The injection was performed over both flow cells at a flow rate of about 60 μl/min. By subtracting the response in flow cell 316 from the response in 314 a referenced response was created free from bulk effects (this provides results that are easier to interpret).

Study the Interaction between p24-Mab and p24

In order to analysis the biomolecular interactions, p24 at 5 μg/ml dissolved in HBS-EP was injected for 3 minutes over both flow cells 314, 316 in the association step; the dissociation step was similarly studied for 3 minutes. A total of six different Mabs were studied where one was run in duplicate to check its repeatability.

Regeneration

Between each injection of Mab, the capturing surface was regenerated for 2 minutes with 10 mM glycine pH 1.8 (i.e., all captured p24-Mab and p24-protein were washed away).

Results

Figure 6:
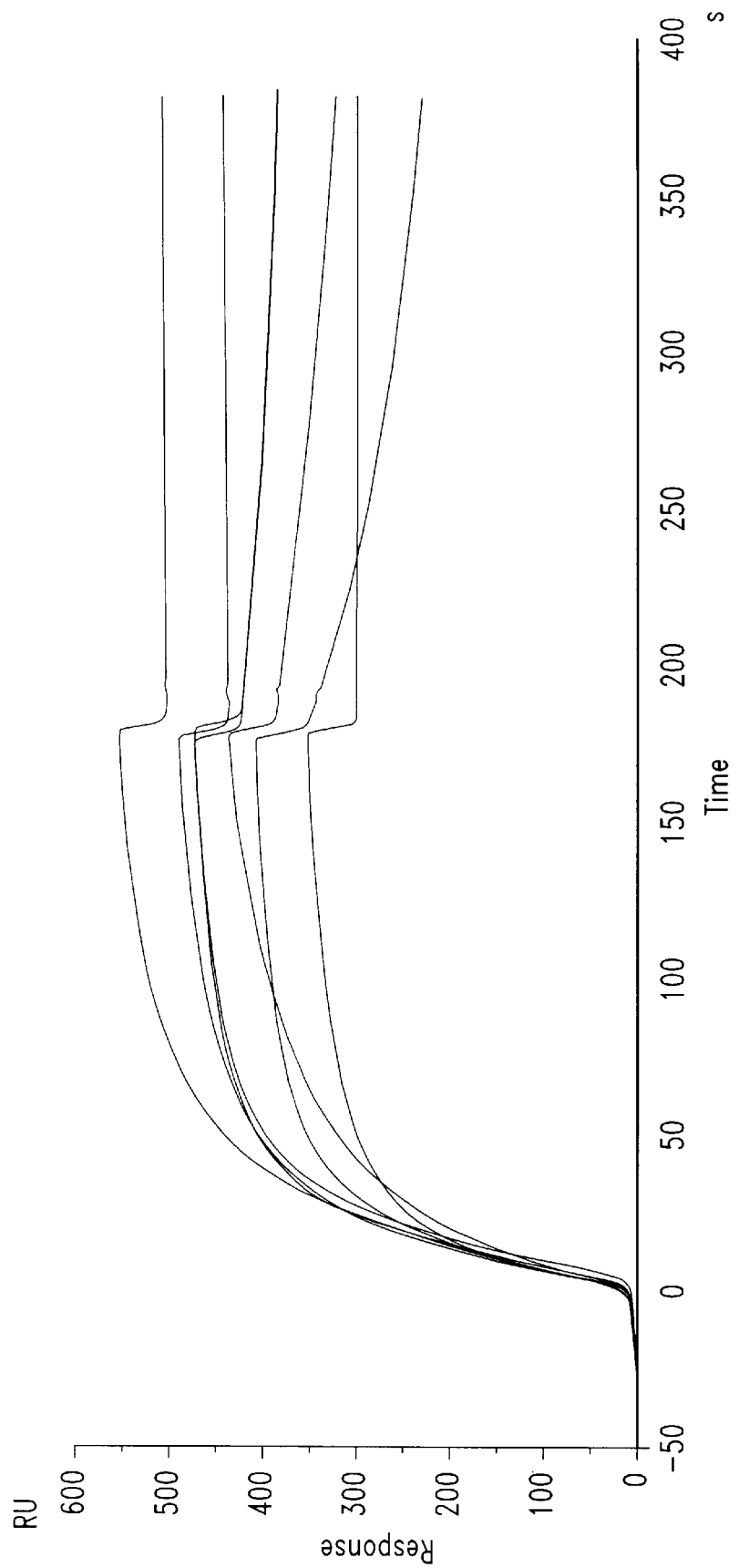
FIG. 6 is an overlay plot of showing some of the relevant data of FIG. 4

The results of this experiment are shown in FIGS. 5 and 6. More specifically, FIG. 5 shows the capturing, p24-interaction, and regeneration for all seven Mabs tested, while FIG. 6 shows an overlay plot of the Mab-p24 interaction showing large variations (especially in dissociation rate). From FIG. 6, three Mabs with low dissociation rates are readily identified.

While the products and methods of the present invention have been described in the context of the embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is, therefore, indicated by the appended claims rather than by the foregoing description, and all changes that come within the meaning and range of equivalency of the claims are to be embraced within their scope.

We claim:

1. A reversible-flow conduit system for contacting a first and second fluid with one or more discrete sensing surfaces of a biosensor, comprising:

a flow-cell conduit having first and second inlet/outlet ports at respective first and second end portions of the flow-cell conduit, wherein the first inlet/outlet port is adapted to receive a the first fluid or expel the second fluid and the second inlet/outlet port is operatively connected to a valveless juncture, and wherein the flow-cell conduit is adapted to flow the first and second fluid in either a first or second flow direction, and in a manner such that the first and second fluid are capable of separately contacting the one or more discrete sensing surfaces of the biosensor, wherein the first flow direction corresponds with a first flow path defined by a flow from the first inlet/outlet port to the second inlet/outlet port, and wherein the second flow direction corresponds with a second flow path defined by a flow from the second inlet/outlet port to the first inlet/outlet port;

a single-fluid conduit adapted to flow therein the second fluid in the second flow direction, wherein the single-fluid conduit has first and second single-fluid conduit end portions, wherein the first single-fluid conduit end portion is operatively connected to the valveless juncture to thereby allow passage of the second fluid there-through;

a two-fluid conduit adapted to simultaneously flow therein the first and second fluid in the first flow direction, wherein the two-fluid conduit has first and second two-fluid conduit end portions, wherein the first two-fluid conduit end portion is operatively connected to the valveless juncture to thereby allow passage of the first and second fluid there-through; and a selector valve having first and second positions adapted to controllably reverse the flow direction of the first and second fluids in the flow-cell conduit, wherein the selector valve is interposed between the end portions of two-fluid conduit, and wherein the first fluid is capable of continuously flowing in the flow-cell conduit in the first flow direction when the selector valve is in the first position, and wherein the second fluid is capable of continuously flowing in the flow-cell conduit in the second direction when the selector valve is in the second position.

2. The reversible-flow conduit system of claim 1, further comprising a pump adapted to flow the first and second fluids, wherein the pump is operatively connected to the second portion end of the two-fluid conduit and the second end portion of the single-fluid conduit.

3. The reversible-flow conduit system of claim 2 wherein the pump is a peristaltic pump having a first and second pumping channel, and wherein the first pumping channel is operatively connected to the second end portion of the two-fluid conduit and the second pumping channel is operatively connected to the second end portion of the single-fluid conduit.

4. The reversible-flow conduit system of claim 2 wherein the pump comprises a plurality of syringe pumps, wherein a first of the plurality of pumps is operatively connected to the second end portion of the two-fluid conduit and a second of the plurality of pumps is operatively connected to the second end portion of the single-fluid conduit.

5. The reversible-flow conduit system of claim 1 wherein the volumetric flow rate capacity of the two-fluid conduit equals the sum of the volumetric flow rate capacity of the flow-cell conduit and the single-fluid conduit.

6. The reversible-flow conduit system of claim 5 wherein the volumetric flow rate capacity of the flow-cell conduit equals the volumetric flow rate capacity of the single-fluid conduit.

7. The reversible-flow conduit system of claim 6 wherein two-fluid conduit has a volumetric flow rate capacity of about 50 μl/min and the single-fluid conduit has a volumetric flow rate capacity of about 25 μl/min.

8. The reversible-flow conduit system of claim 7 wherein the first inlet/outlet port of the flow-cell conduit is adapted to engageably receive a pipette tip.

9. The reversible-flow conduit system of claim 8 wherein the first fluid is a sample solution having an analyte of interest and the second fluid is a buffer solution.

10. The reversible-flow conduit system of claim 1, further comprising a waste-fluid conduit adapted to flow a waste fluid in a continuous manner within the reversible-flow conduit system, wherein the waste-fluid conduit has first and second waste-conduit end portions, wherein the first waste-fluid conduit end portion is operatively connected to the selector valve such that the waste fluid circularly flows within the reversible-flow conduit system when the selector valve is in the second position.

11. A method for reversing the flow direction of a fluid in a flow-cell of a biosensor, comprising the following steps:

(a) providing the reversible-flow conduit system of claim 1 having a first or second fluid flowing within the flow-cell conduit; and (b) reversing the flow direction of either the first or second fluid flowing within the flow-cell conduit by actuating the selector valve.

12. A reversible-flow conduit system for contacting a first and second fluid with one or more discrete sensing surfaces of a biosensor, comprising:

a flow-cell conduit means having first and second inlet/outlet ports at respective first and second end portions of the flow-cell conduit, wherein the first inlet/outlet port is for receiving a liquid sample or expelling a liquid waste and the second inlet/outlet port is operatively connected to a valveless juncture means, and wherein the flow-cell conduit means is for flowing the first and second fluid in either a first or second flow direction within the reversible-flow conduit system, and in a manner such that the first and second fluid are capable of separately contacting the one or more discrete sensing surfaces of the biosensor, wherein the first flow direction of the reversible-flow conduit system corresponds with a first flow path defined by a flow from the first inlet/outlet port to the second inlet/outlet port, and wherein the second flow direction of the reversible-flow conduit system corresponds with a second flow path defined by a flow from the second inlet/outlet port to the first inlet/outlet port;

a single-fluid conduit means for flowing therein the second fluid in the second flow direction within the reversible-flow conduit system, wherein the single-fluid conduit means has first and second single-fluid conduit end portions, wherein the first single-fluid conduit end portion is operatively connected to the valveless juncture means to thereby allow passage of the second fluid there-through;

a two-fluid conduit means for simultaneously flowing therein the first and second fluid in the first flow direction within the reversible-flow conduit system, wherein the two-fluid conduit has first and second two-fluid conduit end portions, wherein the first two-fluid conduit end portion is operatively connected to the valveless juncture means to thereby allow passage of the first and second fluid there-through; and a selector valve means having first and second positions for controllably reversing the flow direction of the first and second fluids in the flow-cell conduit means, wherein the selector valve means is interposed between the end portions of two-fluid conduit means, and wherein the first fluid is capable of continuously flowing in the flow-cell conduit means in the first flow direction when the selector valve means is in the first position, and wherein the second fluid is capable of continuously flowing in the flow-cell conduit means in the second direction when the selector valve is in the second position.

13. The reversible-flow conduit system of claim 12 further comprising a pumping means for flowing the first and second fluids, wherein the pumping means is operatively connected to the flow-cell flow channel means.

14. The reversible-flow conduit system of claim 12 wherein the volumetric flow rate capacity of the two-fluid flow channel means equals the sum of the volumetric flow rate capacity of the flow-cell flow channel means and the single-fluid flow channel means.

15. The reversible-flow conduit system of claim 14 wherein the volumetric flow rate capacity of the flow-cell flow channel means equals the volumetric flow rate capacity of the single-fluid flow channel means.

16. The reversible-flow conduit system of claim 15 wherein two-fluid flow channel means has a volumetric flow rate capacity of about 50 μl/min and the single-fluid flow channel means has a volumetric flow rate capacity of about 25 μl/min.

17. The reversible-flow conduit system of claim 16 wherein the first inlet/outlet port of the flow-cell flow channel means is adapted to engageably receive a pipette tip.

18. The reversible-flow conduit system of claim 17 wherein the first fluid is a sample solution having an analyte of interest and the second fluid is a buffer solution.

19. The reversible-flow conduit system of claim 12, further comprising a waste-fluid conduit means for flowing a waste fluid in a circular manner within the controllable split-flow injection system, wherein the waste-fluid conduit means has first and second waste-conduit end portions, wherein the first waste-fluid conduit end portion is operatively connected to the selector valve means such that the waste fluid circularly flows within the controllable split-flow injection system when the selector valve means is in the second position.

20. A biosensor for detecting biomolecular interations between an analyte and a surface-bound ligand, wherein the biosensor comprises a reversible-flow conduit system for contacting a first and second fluid with one or more discrete sensing surfaces of the biosensor, wherein the reversible-flow conduit system comprises:

- a flow-cell conduit having first and second inlet/outlet ports at respective first and second end portions of the flow-cell conduit, wherein the first inlet/outlet port is adapted to receive a liquid sample or expel a liquid waste and the second inlet/outlet port is operatively connected to a valveless juncture, and wherein the flow-cell conduit is adapted to flow the first and second fluid in either a first or second flow direction within the reversible-flow conduit system, and in a manner such that the first and second fluid are capable of separately contacting the one or more discrete sensing surfaces of the biosensor, wherein the first flow direction of the reversible-flow conduit system corresponds with a first flow path defined by a flow from the first inlet/outlet port to the second inlet/outlet port, and wherein the second flow direction of the reversible-flow conduit system corresponds with a second flow path defined by a flow from the second inlet/outlet port to the first inlet/outlet port;
- a single-fluid conduit adapted to flow therein the second fluid in the second flow direction within the reversible-flow conduit system, wherein the single-fluid conduit has first and second single-fluid conduit end portions, wherein the first single-fluid conduit end portion is operatively connected to the valveless juncture to thereby allow passage of the second fluid there-through;
- a two-fluid conduit adapted to simultaneously flow therein the first and second fluid in the first flow direction within the reversible-flow conduit system, wherein the two-fluid conduit has first and second two-fluid conduit end portions, wherein the first two-fluid conduit end portion is operatively connected to the valveless juncture to thereby allow passage of the first and second fluid there-through; and
- a selector valve having first and second positions adapted to controllably reverse the flow direction of the first and second fluids in the flow-cell conduit, wherein the selector valve is interposed between the end portions of two-fluid conduit, and wherein the first fluid is capable of continuously flowing in the flow-cell conduit in the first flow direction when the selector valve is in the first position, and wherein the second fluid is capable of continuously flowing in the flow-cell conduit in the second direction when the selector valve is in the second position.

* * * * *